(12) United States Patent
Feldman et al.

(10) Patent No.: US 7,540,680 B2
(45) Date of Patent: Jun. 2, 2009

(54) ABRASIVE INJURY CLEANING SYSTEM

(76) Inventors: Joshua Bradley Feldman, 111 W. Main St., Bay Shore, NY (US) 11706; Harriet Feldman, 111 W. Main St., Bay Shore, NY (US) 11706; Howard Sutkin, 111 W. Main St., Bay Shore, NY (US) 11706

( * ) Notice: Subject to any disclaimer, the term of this patent is extended or adjusted under 35 U.S.C. 154(b) by 0 days.

(21) Appl. No.: 11/876,873

(22) Filed: Oct. 23, 2007

(65) Prior Publication Data

US 2009/0103969 A1    Apr. 23, 2009

(51) Int. Cl.
*B43M 11/06* (2006.01)
*A47L 1/08* (2006.01)

(52) U.S. Cl. .................. 401/183; 401/23; 401/24; 401/34

(58) Field of Classification Search .............. 401/183, 401/287, 6, 11, 25, 27, 139, 17, 23, 24, 34; 15/144, 167.3
See application file for complete search history.

(56) References Cited

U.S. PATENT DOCUMENTS

| | | | | |
|---|---|---|---|---|
| 4,730,949 A | * | 3/1988 | Wilson | 401/132 |
| 4,859,102 A | * | 8/1989 | Chamieh | 401/17 |
| 5,035,468 A | * | 7/1991 | Brown et al. | 300/21 |
| 5,163,200 A | * | 11/1992 | Carlin et al. | 15/104.92 |
| 5,312,197 A | * | 5/1994 | Abramson | 401/6 |
| 5,397,194 A | * | 3/1995 | Yuan et al. | 401/186 |
| 6,821,043 B2 | * | 11/2004 | Teh | 401/39 |
| 7,008,132 B1 | * | 3/2006 | Phua et al. | 401/125 |
| 2001/0029967 A1 | * | 10/2001 | McDonough | 134/6 |
| 2004/0154118 A1 | * | 8/2004 | Bohn | 15/114 |

* cited by examiner

*Primary Examiner*—David J Walczak
(74) *Attorney, Agent, or Firm*—Gregory L. Thorne; Thorne & Halajian, LLP

(57) ABSTRACT

A brush system including a brush body, bristles attached to the brush body, and a sponge attached to another part of the brush body. The brush system is arranged to dispense at least two of a topical numbing agent, an antiseptic, and a washing solution. The topical numbing agent is adhered to a surface of the sponge to facilitate applying the topical numbing agent if the surface of the sponge is rubbed onto another surface. The brush body may be arranged to dispense the washing solution in proximity to the bristles if a scrubbing force is applied to the bristles. A bladder may be positioned below the bristles and may be arranged to contain the washing solution. The bristles may contain a channel generally deposed within the bristles. The channels may act as a via between the solution contained within the bladder and an outside surface of the bristles.

14 Claims, 2 Drawing Sheets

ABRASIVE INJURY CLEANING SYSTEM

FIELD OF THE INVENTION

The present system relates to an abrasive injury cleaning system and particularly an abrasive injury cleaning system that is in a form of a multipurpose device.

BACKGROUND OF THE INVENTION

Accidental trauma that breaks the protective outer layer of the skin is common in everyday life. Any break in the skin, regardless of cause, gives bodily access to foreign pathogens, providing a fertile breeding ground and a potential site for serious infection. Preventing infection is critical to the successful healing of any wound, since infection not only lengthens healing time and treatment costs, but also may cause serious, and sometimes life-threatening, complications.

This problem is exacerbated when the injury is a result of a traumatic contact with a hard, dirty surface, such as a roadway. The abrasive contact typical of these types of injuries, such as a result of a motorcycle accident, typically embeds pieces of grit, dirt, and other foreign debris into the abraded surface of the skin making it even more difficult to properly clean the injured area. This foreign debris, which of itself creates a substantial risk of infection, may be left in the wound after the skin has healed. This type of traumatic injury, without proper debriding of the wound, may result in a condition called traumatic tattooing. In traumatic tattooing, a pigmented foreign particle is impregnated within the dermal layer of the skin, which during the healing process, takes on the pigment from the foreign particle. Further, the skin may take on a mottled appearance due to the presence of the foreign particle below the outer layer of the skin. Once this occurs, the condition is difficult to correct without causing additional scarring in the area.

Time is an important factor in treating an abrasive or other penetrating skin injury. Skin wounds need to be thoroughly cleaned and debrided as soon as possible to reduce the risk of infection and scarring and to promote healing. A break in the skin that is four hours old before it is treated is significantly more likely to become infected than one that is treated within a half hour of injury occurrence. The longer the time period between skin breakage and treatment, the greater the possibility of infection and long-term scaring. Proper care of a wound includes cleaning and debris removal, ideally, shortly after occurrence of the wound.

Yet, first responders to an incident wherein there is injury typically are busied with responding to the ABC's of injuries, which includes checking that a victim has an airway, is breathing, and has circulation. After confirmation of the ABC's, the first responder may attempt to control bleeding at the injured area. Procedures such as localized pressure and application of a dressing may aid in reducing bleeding at the site but does little to debride a wound or reduce a risk of infection. Victims that are subsequently transported to a medical facility for treatment are typically triaged and are required to wait long periods if the injuries are deemed to not be life threatening. Accordingly, even in a case wherein the victim is seen a short time after a skin injury, the injury typically is not treated till long after the time of occurrence.

Even long after, when the injury is typically cared for, there are no real suitable compact solutions for dealing with the injury. Many types of medical appliances exist that aid in treating tissue injuries, yet do not really aid in debriding the injury. For example, applicators like sponges, cotton swabs or pads may be soaked in an iodine-based solution, such as a providone-iodine solution, to act as an antibacterial agent to facilitate cleaning of injured tissue. Germicidal preparations such as Betadine™, Hibiclens™ and Klenz Gel Blu™ are widely available for cleaning of tissue injuries either with an applicator or in a dispensing container. The applicators are typically sealed in a sterile packaging that is dispensed as a single-use item, which is disposed of after the single-use. The applicator is opened just prior to use and may be utilized to spread the antibacterial agent over the intended site. The applicator may be attached to a handle to facilitate manipulation of the applicator on the injury site. While this system of applying the antibacterial agent over the injury site works well enough to clean the site, the applicator does little to assist in a removal of foreign debris from the site.

It is an object of the present system to overcome disadvantages and/or make improvements in the prior art.

SUMMARY OF THE INVENTION

A brush system including a brush body, bristles attached to the brush body, and a sponge attached to another part of the brush body. The brush system is arranged to dispense at least two of a topical numbing agent, an antiseptic, and a washing solution. In one embodiment, the topical numbing agent is adhered to a surface of the sponge that is arranged to apply the topical numbing agent if the surface of the sponge is rubbed onto another surface. The brush body may be arranged to dispense the washing solution in proximity to the bristles if a scrubbing force is applied to the bristles. A bladder may be positioned below the bristles and may be arranged to contain the washing solution. The bristles may contain a channel generally deposed within the bristles. The channels may act as a via between the solution contained within the bladder and an outside surface of the bristles. In this embodiment, the scrubbing force may compress the bladder which dispenses the washing solution through the channels.

The brush body may be arranged to dispense the antiseptic through the sponge portion if a scrubbing force is applied to the sponge portion. A bladder may be positioned within the sponge portion and may contain the antiseptic. The bladder may include pores arranged to retain the antiseptic in the bladder if the bladder is uncompressed. The pores may dispense the antiseptic if the bladder is compressed. The sponge may contain channels deposed in proximity to the pores through the bladder that each act as a via between the antiseptic contained within the bladder and an outside surface of the sponge portion. In this embodiment, the scrubbing force may compress the bladder to dispense the antiseptic through the channels.

The topical numbing agent may be adhered to a surface of the sponge and the antiseptic may be contained within the sponge. In a case wherein a rubbing force is applied between the surface of the sponge and an other surface, a portion of the topical numbing agent may be transferred to the other surface. If a scrubbing force is applied between the surface of the sponge and the other surface, a portion of the antiseptic contained within the sponge may be transferred to the other surface. The brush system may include both of a first bladder positioned below the plurality of bristles to contain the washing solution, and a second bladder positioned within the sponge portion to contain the antiseptic. The brush system may be contained within a sterile package to maintain an aseptic environment around the brush system.

BRIEF DESCRIPTION OF THE DRAWINGS

It should be expressly understood that the drawings are included for illustrative purposes and do not represent the scope of the present system. The invention is explained in further detail, and by way of example, with reference to the accompanying drawings wherein.

DETAILED DESCRIPTION OF THE INVENTION

The following are descriptions of illustrative embodiments that when taken in conjunction with the following drawings will demonstrate the above noted features and advantages, as well as further ones. In the following description, for purposes of explanation rather than limitation, specific details are set forth such as architecture, structure, etc., for illustration. However, it will be apparent to those of ordinary skill in the art that other embodiments that depart from these details would still be understood to be within the scope of the appended claims. Moreover, for the purpose of clarity, detailed descriptions of well-known portions and methods are omitted so as not to obscure the description of the present system. In the accompanying drawings, like reference numbers in different drawings may designate similar elements, portions of similar elements and/or elements with similar functionality. Objects depicted in the figures are not necessarily drawn to scale and size relationships may be exaggerated for purposes of illustrating operation of the current system.

Figure 1:
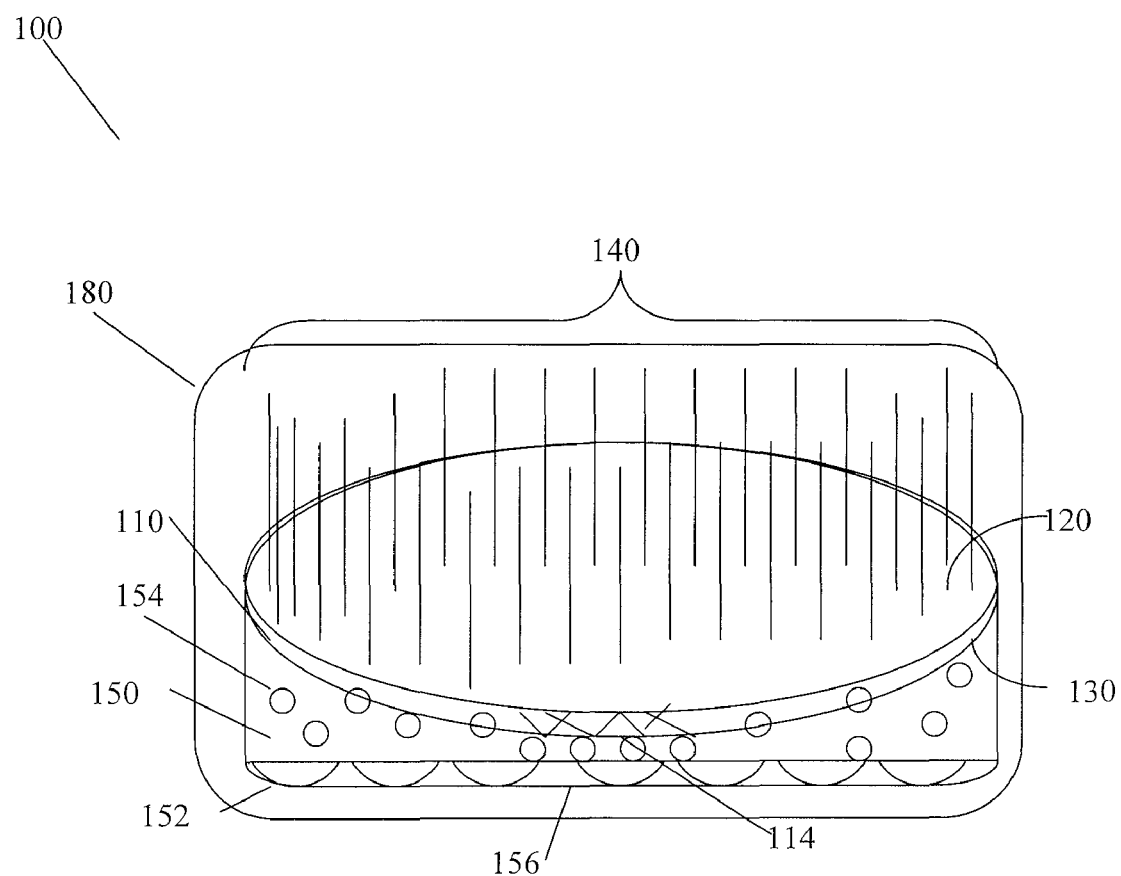
FIG. 1 shows a brush according to an illustrative embodiment of the present system.

FIG. 1 shows a perspective view of a brush system 100 including a brush 110 having a first side 120 and a second side 130. The brush may be formed of a rigid material, such as a plastic material, resin, and/or another synthetic or a natural material as may be readily appreciated. The brush 110 may have a patterned outer surface 114 to facilitate holding and manipulating the brush 110 as described further herein. The patterned outer surface 114 may be knurled, formed, or provided by other suitable means onto the brush 110 surface. The brush 110 may be sized so as to be readily manipulated by one hand. For example, in one embodiment the brush may measure 3 inches long by 2 inches wide. Naturally other dimensions and/or combinations of dimensions for the brush 110 may be utilized in accordance with the present system.

In accordance with the present brush, bristles 140 may be operably affixed to the first side 120 and a porous absorbent material, such as a sponge 150, may be operably affixed to the second side 130 of the brush 110. For example, a base of the bristles 140 may be embedded into the first side 120 of the brush as may be readily appreciated or may be embedded into another surface that is affixed, such as glued, to the first side 120. The sponge 150 may, for example, be glued to the second surface 130. As may be readily appreciated by a person of ordinary skill in the art, other methods of affixing the bristles 140 and the sponge 150 to the brush 110 may be readily applied in accordance with the present system. In one embodiment, the sponge 150 may be formed of a rubber-based compound or may be cellulose-based depending on a desired firmness of the sponge 150. The bristles 140 may be formed of a natural material, such as animal hair (badger, pig, boar, etc.) and/or more be formed from a synthetic material, such as nylon, polyester, and/or other synthetic materials as desired.

The sponge 150 may have a surface 152 that generally rises and falls, for example, producing round contours on the surface 152. The contours on the surface 152 may generally aid in application of a material to a skin surface. However, in another embodiment the surface 152 may be generally flat and/or have other contours as may be readily appreciated by a person of ordinary skill in the art. To facilitate utilizing the surface 152 as an applicator, the surface 152 may be generally compressible as may be typical of a sponge surface although a higher or lower degree of compressibility of the surface 152 may also be desired. For example, a lower degree of compressibility may aid in scrubbing harder with the sponge 150 without the sponge 150 becoming fully compressed.

In one embodiment, the surface 152 may be operable to apply a topical anesthetic 156, such as a gel-agent that is partially adhered to the surface 152. For example, the anesthetic 156 may be lidocaine-based. The anesthetic 156 may be transferred from the surface 152 to a surface, such as a skin area, by application of a rubbing force to the brush 110. A rubbing force, as utilized herein is intended to be a force that is applied to the brush 110 sufficient to break a surface tension between the anesthetic 156 and the skin area, for example, such that the brush may be rubbed in a back-and-forth motion on the skin area. A rubbing force should also be understood to include a force that is sufficient to dab the anesthetic 156 onto the skin area. In operation, the topical anesthetic 156 may be utilized to desensitize an area of skin of a user to enable manipulation of the skin area during treatment with the brush system 100 while reducing discomfort to the user. Other anesthetics may also be suitably utilized, such as anesthetics or analgesics commonly utilized to treat abrasions, cuts, and/or other wounds in accordance with the present system as may be readily appreciated.

The sponge 150 may also be partially saturated with an antibacterial agent 154, such as an iodine-based solution like a providone-iodine solution. In this way, the surface 152 may be partially compressed during application of a scrubbing force to the brush 110 of the brush system 100 which may partially dispense the antibacterial agent 154 to facilitate cleaning and disinfecting of injured tissue. In general, a scrubbing force may be understood to be a larger force than a rubbing force and may cause a slight or greater compression of the sponge 150. By first application of a rubbing force to the brush system 100, thereby dispensing the topical anesthetic 156 previously deposited on the surface 152, followed by application of a scrubbing force dispensing the antibacterial agent 154, an effective disinfecting of the skin area may be performed without causing discomfort to the user.

The brush 110 may be turned over to the second side 120, wherein the bristles 140 are operably affixed, for assistance in removal of foreign matter that is imbedded into the skin of the user. By application of a scrubbing force to the brush over the injured skin area, the bristles 140 may enter a break in the injured skin area to brush away the foreign matter. Due to the anesthetic effect of the previously applied topical anesthetic 156, discomfort typically associated with brushing over the injured area may be greatly reduced. In one embodiment in accordance with the present system, a length of the bristles 140 may vary over portions of the brush 110 such that an uneven brushing surface is presented to the skin area which may further assist in the removal of the foreign matter during brushing. In this embodiment, the foreign matter may be dislodged from the skin by longer bristles and become lodged in a space provided in the brushing surface by the shorter bristles. Further, the different length bristles may assist in scrubbing debris from different depths of an open wound present in the injured skin area. In this embodiment, a wash, such as a sterile saline solution may be dispensed from a sterile container during the scrubbing with the bristles 140 to assist in washing away the foreign debris.

Figure 2:
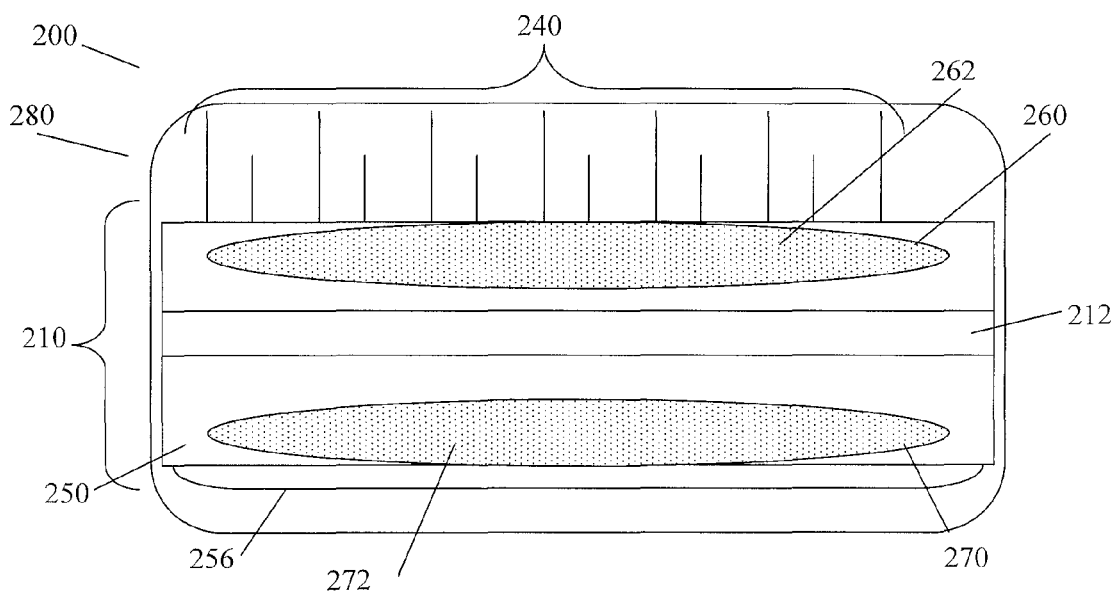
FIG. 2 shows a brush according to another illustrative embodiment of the present system.

FIG. 2 shows a side view 200 of a brush 210 in accordance with an embodiment of the present system. Similar as depicted in FIG. 1, the brush 210 has a surface substantially covered with bristles 240 and a surface covered with a sponge 250. The bristles 240 are shown to have a varying length as discussed previously. A surface of the sponge 250 may be covered with a topical anesthetic 256. In accordance with an embodiment of the present system, the brush 210 may include one or more bladders, such as bladders 260, 270 that are embedded into a surface of the brush 210. For example, the bladder 260 may be arranged to store a washing solution, such as a sterile saline solution. The bladder 260 may have a plurality of pores 262 that are sized and arranged such that when the bladder 260 is uncompressed, the bladder 260 will retain the washing solution. In operation, if a scrubbing force is applied when the bristles 240 are in contact with surface area, such as an injured skin area, the bladder 260 may be completely or partially compressed, thereby dispensing the washing solution through the pores 262, to aid in washing away any foreign debris.

Figure 3:
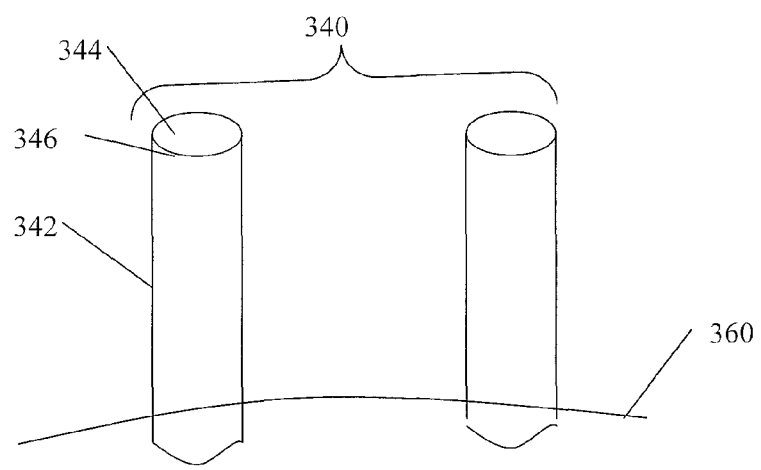
FIG. 3 shows details of a bristle with a channel connected to a bladder in accordance with an embodiment of the present system.

FIG. 3 shows a close-up of a portion of a bladder 360 and bristle arrangement 340 in accordance with an embodiment of the present system. The bladder 360 may be embedded into a brush similar as the brush 210 shown in FIG. 2. In this embodiment, the bristle arrangement 340 may include one or more bristle(s) 342 that have interior channels 344 that pass from an outside portion 346 of the bristle(s) 342 to an interior portion of the bladder 360. The channels 344 may be arranged such as to provide a via for a solution (e.g., cleansing solution) that is stored in the bladder 360. In this embodiment, when the bladder 360 is compressed, such as in application of a scrubbing force to the bristles 340, the channels 344 may carry a portion of the solution to the outside portion 346 of the bristle 340, which may be deposed within an injured skin area, and/or be deposed beneath a surface of the skin area. By the direct application of the solution through the channels 344 onto the injured area, a more effective cleaning of the injured area may be accomplished further facilitating removal of any foreign debris present in and/or within the injured area.

Returning to FIG. 2, a bladder 270 may deposed within the sponge 250. The bladder 270 may contain pores 272 that are sized and arranged to facilitate retention of a solution deposed within the bladder 270. For example, the bladder 270 may contain an antiseptic fluid that is retained within the bladder 270 when the bladder 270 is in an uncompressed state. Thereafter, when a scrubbing force is applied to a surface, such as an injured skin area through the sponge 250, the blabber 270 may be become completely or partially compressed, thereby, dispensing the solution through the pores 272. In this embodiment, an antiseptic fluid may be deposited on the injured skin area to help rid the injured area of bacteria that may have been deposited during an injury. In this embodiment, the sponge 250 may be partially saturated with a same or different solution than is contained within the bladder 270. In an embodiment wherein a different solution is contained within the bladder 270 than is contained within the sponge 250, each solution may be selected to facilitate a different germicidal action and thereby, aid in disinfecting of different bacterium. In another embodiment, the sponge 250 may not be saturated with a solution and the application of an anesthetic contained within the bladder 270 may only be brought about after a compressing force is applied to the bladder 270.

In one embodiment, the brush 210 may contain an isolating portion 212 that is rigid and thereby, isolates one side of the brush from another. In this way, application of a force, for example, pushing the sponge 250 down onto a surface (e.g., injury site), will not cause a depression of the bladder 260 deposed on the bristle side of the brush 210. This embodiment of the brush may be utilized regardless of whether one or more bladders are present in the brush system to, for example, aid in squeezing or not squeezing of the sponge 250 when desired or not desired, such as when the bristles 240 are being utilized for debridement. In this embodiment, the brush 210 may be generally formed from a flexible material, such as a polyvinyl material, with the exception of the isolating portion 212, which may be formed from a rigid material, such as a plastic or metal material.

Prior to use, the brush system, such as shown in any of FIGS. 1-3, may be stored in a sealed packaging 180, 280 that has a sterilized interior. The brush system may be similarly sterilized or simply be prepared in an sterile environment to avoid contamination (e.g., germs, dirt, grit, etc) before insertion into the packaging so that the brush system may remain generally aseptic prior to opening of the sterilized packaging. In this way, the brush system may be provided as a single-use product, that is aseptic prior to use and that may be disposed of after use. Through use of the present brush system, an effective tool for management of an injury is provided in a compact single item, which when utilized may provide relief from pain at the injury site, cleaning and disinfecting of the injury, as well as effective debridement of any open wounds. Since the brush system is compact, it may be deployed to first responders to provide an effective system for caring for an injury prior to transportation of an accident victim to a medical facility thereby, increasing the chances that the injury will be cleaned and debrided a relatively short period of time after occurrence of the injury. By use of the present brush system, the injury may be properly cleaned and cared for greatly reducing a risk of developing an infection or long term scarring of the injured area.

Of course, it is to be appreciated that in accordance with the present system, any one of the above, elements, embodiments and/or processes may be combined with one or more other elements, embodiments and/or processes. For example, vias may be present in the sponge to facilitate deposition of a solution, such as an antiseptic agent, contained in the bladder onto an injured site (e.g., skin area). Further, the anesthetic may be suspended within the sponge as opposed to adhered to an outer surface of the sponge, for example if a liquefied topical anesthetic is utilized in place of a gel topical anesthetic. In one embodiment, the antiseptic may be contained within a bladder, such as the bladder 270, for deposition after the anesthetic that is suspended in the sponge is generally squeezed out of the sponge. Accordingly, numerous combinations would readily occur to a person of ordinary skill in the art. These and other variations should be understood to be within the scope of the presented claims. As should be clear from the discussion herein, the present system overcomes disadvantages and/or makes improvements over other systems.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise; and h) no specific sequence of acts or steps is intended to be required unless specifically indicated.

The claimed invention is:

1. A brush system comprising:
a brush body including a first surface and a second surface opposing the first surface;
a plurality of bristles operably coupled to the first surface in proximity to each other and extending outward from the brush body;
a sponge portion operably coupled to the second surface and extending outward from the brush body;
a topical numbing agent adhered to a surface of the sponge, wherein the surface of the sponge applies the topical numbing agent if the surface of the sponge is rubbed onto another surface; and
at least one of an antiseptic and a washing solution, wherein the brush system is structured for separately dispensing the topical numbing agent and the at least one of the antiseptic and the washing solution.

2. The brush system of claim 1, comprising the washing solution, wherein the brush body dispenses the washing solution in proximity to the first surface if a scrubbing force is applied to the plurality of bristles.

3. The brush system of claim 2, comprising
a bladder positioned below the plurality of bristles and containing the washing solution.

4. The brush system of claim 3, wherein the plurality of bristles each contain a channel generally deposed within the bristles that each act as a via between the solution contained within the bladder and an outside surface of the bristles, and wherein the scrubbing force compresses the bladder which dispenses the washing solution through the channels.

5. The brush system of claim 1, wherein the brush system comprises the antiseptic and wherein the brush body dispenses the antiseptic through the sponge portion if a scrubbing force is applied to the sponge portion.

6. The brush system of claim 5, comprising a bladder positioned within the sponge portion and containing the antiseptic.

7. The brush system of claim 6, wherein the bladder comprises pores sized to retain the antiseptic in the bladder if the bladder is uncompressed and to dispense the antiseptic if the bladder is compressed, wherein the plurality of bristles contain channels deposed in proximity to the pores through the bladder that each act as a via between the antiseptic contained within the bladder and an outside surface of the plurality of bristles, and wherein the scrubbing force compresses the bladder which dispenses the antiseptic through the channels.

8. The brush system of claim 1, wherein the brush system comprises the antiseptic contained within the sponge portion, wherein if a rubbing force is applied between the surface of the sponge and an other surface, a portion of the topical numbing agent is transferred to the other surface, and wherein if a scrubbing force is applied between the surface of the sponge and the other surface, a portion of the antiseptic contained within the sponge is transferred to the other surface.

9. The brush system of claim 1, comprising:
the washing solution;
the antiseptic;
a first bladder positioned below the plurality of bristles and containing the washing solution; and
a second bladder positioned within the sponge portion and containing the antiseptic.

10. The brush system of claim 1, comprising a sterile package positioned around the brush body, the plurality of bristles and the sponge portion, wherein the sterile package is sealed to maintain an aseptic environment around the brush body, the plurality of bristles and the sponge portion.

11. The brush system of claim 1, comprising:
a first bladder positioned below the plurality of bristles;
a second bladder positioned within the sponge portion; and
a rigid surface positioned between the first bladder and the second bladder, wherein the rigid surface isolates the first bladder from a compressing force if the compressing force is applied to the second surface, and wherein the rigid surface isolates the second bladder from the compressing force if the compressing force is applied to the first surface.

12. The brush system of claim 1, comprising:
the antiseptic; and
a bladder positioned within the sponge portion, wherein the antiseptic is a first antiseptic, the brush system comprising a second antiseptic, wherein the blabber contains the first antiseptic and wherein the sponge portion is partially saturated with the second antiseptic.

13. A brush system comprising:
a brush body including a first surface and a second surface opposing the first surface;
a plurality of bristles operably coupled to the first surface in proximity to each other and extending outward from the brush body;
a sponge portion operably coupled to the second surface and extending outward from the brush body;
at least two of a topical numbing agent, an antiseptic, and a washing solution, wherein one of the topical numbing agent, antiseptic and washing solution is adhered to a surface of the sponge, wherein the brush system is structured for separately dispensing the least two of the topical numbing agent, the antiseptic, and the washing solution; and
a sterile package positioned around the brush body, the plurality of bristles and the sponge portion, wherein the sterile package is sealed to maintain an aseptic environment around the brush body, the plurality of bristles and the sponge portion.

14. A brush system comprising:
a brush body including a first surface and a second surface opposing the first surface;

a plurality of bristles operably coupled to the first surface in proximity to each other and extending outward from the brush body;

a sponge portion operably coupled to the second surface and extending outward from the brush body;

at least two of a topical numbing agent, an antiseptic, and a washing solution, wherein the brush system is structured for separately dispensing the least two of the topical numbing agent, the antiseptic, and the washing solution; and a first bladder positioned below the plurality of bristles;

a second bladder positioned within the sponge portion; and a rigid surface positioned between the first bladder and the second bladder, wherein the rigid surface isolates the first bladder from a compressing force if the compressing force is applied to the second surface, and wherein the rigid surface isolates the second bladder from the compressing force if the compressing force is applied to the first surface.

* * * * *